(12) United States Patent
Yazdani et al.

(10) Patent No.: US 10,281,511 B2
(45) Date of Patent: May 7, 2019

(54) PASSIVE WIRELESS SENSOR FOR THE MEASUREMENT OF AC ELECTRIC FIELD IN THE VICINITY OF HIGH VOLTAGE APPARATUS

(71) Applicant: University Of Manitoba, Winnipeg (CA)

(72) Inventors: Mana Yazdani, Winnipeg (CA); Behzad Kordi, Winnipeg (CA); Douglas J. Thomson, Winnipeg (CA)

(73) Assignee: The University of Manitoba, Winnipeg (CA)

( * ) Notice: Subject to any disclaimer, the term of this patent is extended or adjusted under 35 U.S.C. 154(b) by 64 days.

(21) Appl. No.: 15/526,566

(22) PCT Filed: Nov. 13, 2015

(86) PCT No.: PCT/CA2015/051188
§ 371 (c)(1),
(2) Date: May 12, 2017

(87) PCT Pub. No.: WO2016/074100
PCT Pub. Date: May 19, 2016

(65) Prior Publication Data
US 2017/0322246 A1    Nov. 9, 2017

Related U.S. Application Data

(60) Provisional application No. 62/079,063, filed on Nov. 13, 2014.

(51) Int. Cl.
*G01R 29/08* (2006.01)
*G01D 5/14* (2006.01)
*G01N 27/24* (2006.01)
*G01R 15/26* (2006.01)
*G01R 19/25* (2006.01)

(52) U.S. Cl.
CPC ........... *G01R 29/0814* (2013.01); *G01D 5/14* (2013.01); *G01N 27/24* (2013.01); *G01R 15/26* (2013.01); *G01R 19/2513* (2013.01); *G01R 29/0878* (2013.01)

(58) Field of Classification Search
CPC ....... G01R 19/2513; G01R 15/26; G01D 5/14
See application file for complete search history.

(56) References Cited

U.S. PATENT DOCUMENTS

2005/0241403 A1* 11/2005 Thomson ................ E01D 19/00
                                                                    73/773
2007/0030134 A1*  2/2007 Liu ............................ G01L 3/10
                                                                    340/441

(Continued)

*Primary Examiner* — Giovanni Astacio-Oquendo
*Assistant Examiner* — Alvaro E Fortich
(74) *Attorney, Agent, or Firm* — Carlson, Gaskey & Olds, P.C.

(57) ABSTRACT

A new passive wireless electric field sensor is disclosed. This sensor does not require direct attachment to a source of power which makes it passive. It is composed of a resonator loaded with varactors. The sensor is interrogated by a remotely located device transmitting and receiving the pulses of sine wave in the resonance frequency range of the sensor. Therefore, the sensor can be mounted in the vicinity of high voltage apparatus and interrogated from a safe distance.

21 Claims, 12 Drawing Sheets

(56) References Cited

U.S. PATENT DOCUMENTS

| | | | |
|---|---|---|---|
| 2009/0001850 A1* | 1/2009 | Kalinin | G01L 1/165 310/313 R |
| 2010/0219494 A1* | 9/2010 | Barnaby | B82Y 15/00 257/429 |
| 2010/0250170 A1* | 9/2010 | Kalinin | B60C 23/0408 702/77 |
| 2013/0106447 A1* | 5/2013 | Bridges | G01N 17/04 324/700 |

* cited by examiner

PASSIVE WIRELESS SENSOR FOR THE MEASUREMENT OF AC ELECTRIC FIELD IN THE VICINITY OF HIGH VOLTAGE APPARATUS

CROSS-REFERENCE TO RELATED APPLICATION

This application is a non-provisional application from 62/079,063 filed Nov. 13, 2014 the entirety of which is hereby incorporated by reference for all purposes.

TECHNICAL FIELD

The present disclosure relates to passive sensors and in particular to measurement of high voltage AC electric fields using a passive sensor.

BACKGROUND

The increasing demand for electric power over the last decade has urged the high voltage apparatus to operate at full load while the power systems are expected to provide high quality and reliable electric power. On the other hand, the increasing dependence on the electricity has increased the cost of power outages and quality disturbances. In order to avoid power outages and disturbances caused by equipment failures and outages, online distributed and low-cost condition monitoring, diagnostics and protections are crucial in modern power systems.

Electric field measurement in the vicinity of high voltage apparatus is part of condition monitoring and protection in power systems. Determining the electric-field distribution profile surrounding a high voltage equipment provides reliability information about the insulation condition.

Most recent efforts in the development of electric field measurement sensors have been towards optical sensors. These sensors convert electrical signals to optical signals based on the Pockels or piezoelectric effects. The most significant advantage of these sensors is that they do not require any contact to the high voltage apparatus, which makes them portable measurement devices and also eliminates the source loading and power dissipation. Further, the all-fiber structure of these sensors minimizes the risk of flash over and provides electric isolation from the high voltage apparatus. Although these sensors are considered portable measurement devices, the weight of the optical voltage measurement structures known as optical voltage transducers is considerably high. The information received from these sensors is transmitted by optical rays through fiber optic cables. They are considered as active sensors which require external source of power and safety precautions for installation. Accordingly, systems and methods that enable measurement of high voltage AC electric fields remains highly desirable.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Embodiments are described below, by way of example only, with reference to FIGS. 1-12.

In accordance with an aspect of the present disclosure there is provided a method of measurement of AC electric field in the vicinity of high voltage apparatus, the method comprising transmitting radio frequency (RF) sine wave pulses to a passive sensor placed within an AC electric field; receiving an RF ring back signal from the sensor; determining a resonance frequency of the sensor; determining a reverse bias voltage of the inducing electric field from the received RF ring back signal and the determined resonate frequency; and determining an electric field measurement value from the determined bias voltage.

In accordance with another aspect of the present disclosure there is provided a passive sensor for measurement of AC electric field in the vicinity of high voltage apparatus, the resonator comprising an inner cylinder and an outer cylinder comprising a coaxial cavity resonator having an air filled gap; a top surface comprises a printed circuit board material having a varactor thereon spanning a ring gap surrounding an isolated region coupling the inner and outer cylinders; and a coaxial connector on the outer cylinder for coupling to an antenna for receiving a wireless signal wherein the wireless signal comprising RF pulses for generating a ring back signal for measuring of the AC electric field.

In accordance with yet another aspect of the present disclosure there is provided a system for measuring a high voltage AC electric field of a high voltage apparatus, the method comprising a passive AC electric field sensor, placed in proximity to an AC electric field, for receiving RF pulses and generating a ring back signal; and an interrogator system for generating RF pulses wireless sent to the passive AC electric field sensor and receiving the ring back signal from the passive AC electric field sensor and determining an electric field value for an inducing electric field.

A new passive, wireless electric field sensor is provided. The sensor is composed of an RF resonator loaded with varactors that is wirelessly interrogated by sending and receiving RF pulses with a frequency close to the resonance frequency. None of the currently employed sensors for the measurement of the electric field in the vicinity of high voltage apparatus, are passive and wireless. Further, the available passive wireless electric field sensors are generally used in short distance measurement of stationary measurands. The disclosed sensor is passive thus there is no need for batteries. Interrogation of the sensor is done wirelessly from a safe distance and no grounding is required thus the risk of flash-over is reduced. Interrogation has a fast sampling rate which is capable of measuring variations in ms (potentially µs) range. The sensors are light and inexpensive allowing distributed electric field measurement and the interrogation method has the potential of extending the interrogation distance and simultaneous measurement of multiple sensors. The electric field measurement determined from the sensor can be used for insulation defect detection or voltage measurement using a few sensors surrounding the high voltage apparatus and deriving the voltage on the apparatus by deriving the electric field profile.

The passive sensor does not require direct attachment to a source of power which makes it passive. It is composed of a resonator loaded with varactors. The sensor is interrogated by a remotely located device transmitting and receiving the pulses of sine wave in the resonance frequency range of the sensor. Therefore, the sensor can be mounted in the vicinity of high voltage apparatus in the 200 V/m to 7 kV/m range for a resolution of 12.5 V/m interrogated from a safe distance. The measurable range of the electric field is dependent on the resonator dimensions, the varactors, and the resistors in parallel to the varactors. The sensor structure is adaptable to different measurement scenarios and the same procedure as described can be applied to adjust the sensor to different environments.

Figure 1:
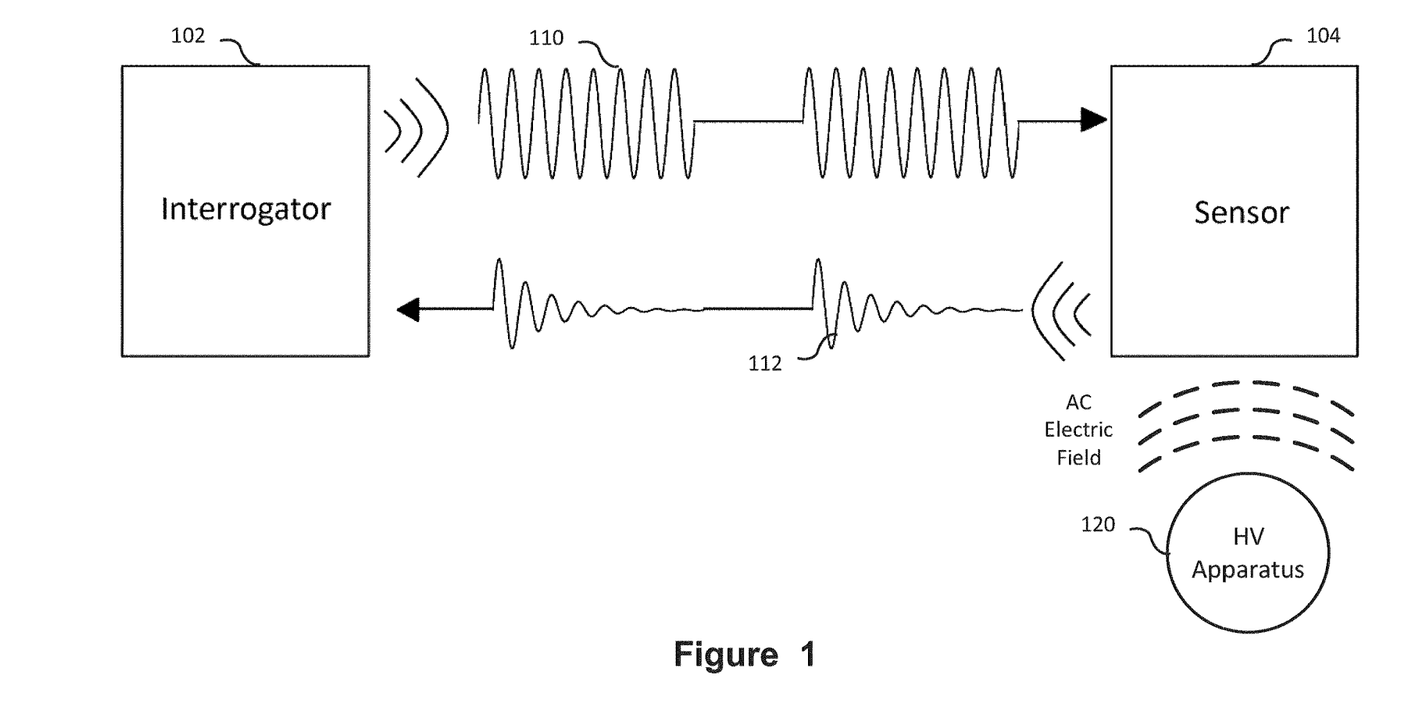
FIG. 1 shows transmitting pulses of sine wave and receiving the resonator ring back on the interrogator.

Referring to FIG. 1, the operation of the sensor 104 is based on the fact that the external electric field (E) from high voltage apparatus 120 can induce a bias voltage on the varactors, which in turn varies the capacitance of the resonator in sensor 104. Variation of the capacitance will change the resonance frequency. An interrogator 102 can detect the change in the resonance frequency. The interrogation is performed by sending short pulses 110 of a sine wave and receiving the response of the resonator in the sensor 104. The response comprises of damping sine wave pulses 112 referred to as the ring back of the resonator which has the frequency equal to the resonance frequency.

The electric field sensor 104 is composed of a radio frequency transmission line coaxial cavity resonator that is capacitively coupled to varactors. A change in the capacitance of the varactors causes a shift in the resonance frequency. An external AC electric field induces a bias voltage over the terminals of the varactors which in turn varies the resonance frequency of the resonator. The interrogator 102 detects the shift in the resonance frequency and hence the value of the external electric field. In the interrogation method provided RF pulses are transmitted excite the coaxial cavity resonator in the transverse mode (TEM) mode and the response of the resonator is received as shown in FIG. 1. The response is a damped sine wave which is referred to as the ring back of the resonator whose frequency is equal to the natural frequency of the resonator.

Figure 2:
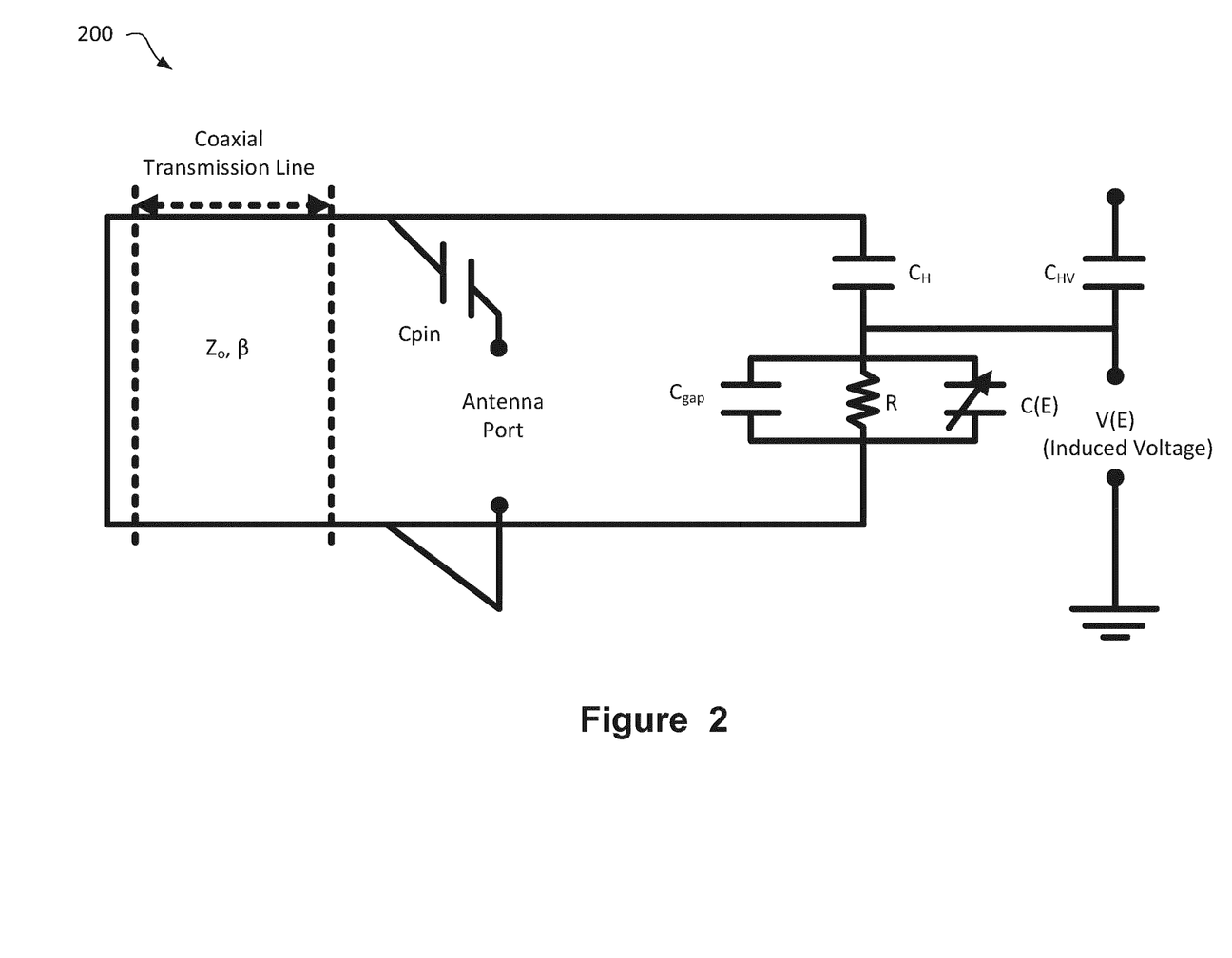
FIG. 2 shows the equivalent circuit model of the coaxial cavity.
Figure 3:
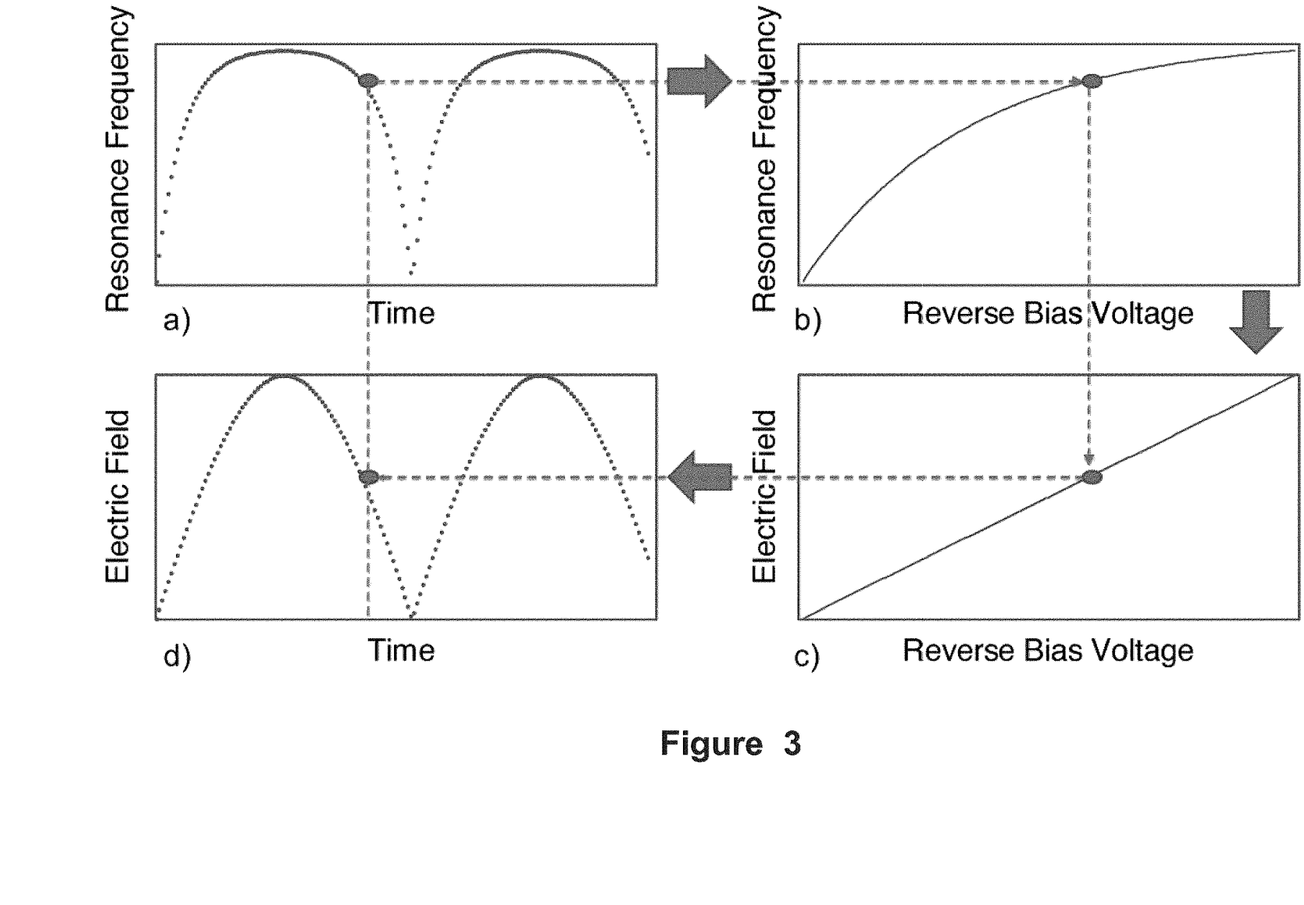
FIG. 3 shows mapping the derived resonance frequency to the corresponding electric field amplitude.

FIG. 2 shows the equivalent circuit model 200 of the coaxial cavity resonator in sensor 104 consisting of a TEM mode coaxial transmission line short circuited at one end and capacitively loaded at the other. The potential over the varactor is capacitively induced by the high voltage. At the top of the sensor, an isolated region is formed on a printed circuit board (PCB) and the varactors bridge across the gap between this isolated region and the surrounding conductor. The external AC electric field is also capacitively coupled to this isolated region inducing a potential across the varactors. The isolated region forms a parasitic capacitance that is in parallel to the varactor (Cgap) and in series with the capacitive load of the air gap ($C_H$). The variation of the external AC electric field changes the capacitance of the varactors, which in turn changes the capacitive loading seen by the resonator and consequently its resonance frequency.

In order to measure the electric field strength surrounding the sensor, the resonance frequency of the sensor/resonator must be measured. A representation of the procedure of mapping each resonance frequency to the corresponding electric field is illustrated in FIGS. 3a-d. The result of the measurement is a graph of the resonance frequency variation in time as is shown in FIG. 3a. Then, by mapping this resonance frequency to the corresponding reverse bias voltage over the varactors, the bias voltage is derived which itself indicates the inducing electric field. By mapping this resonance frequency to the corresponding reverse bias voltage over the varactors, the bias voltage is derived which can then be mapped to the inducing electric field. The graph in FIG. 3b, which shows the variation of the resonance frequency versus the reverse bias voltage of the varactor, is derived using S-parameter measurement of the resonator and FIG. 3c is derived using finite element simulation. FIG. 3d shows the absolute value of the electric field sampled in time.

Measurement of an AC electric field requires fast determination of the resonance frequency by the interrogation system. A typical high voltage device operates in 50/60 Hz frequency with a 20/16.67 milliseconds period. In practice, to have an accurate interrogation, the number of samples taken from the 50/60 Hz signal must be at least 10 samples per cycle corresponding to a sampling frequency of 500/600 samples/s. Higher AC field frequencies require higher sampling rates.

Figure 4:
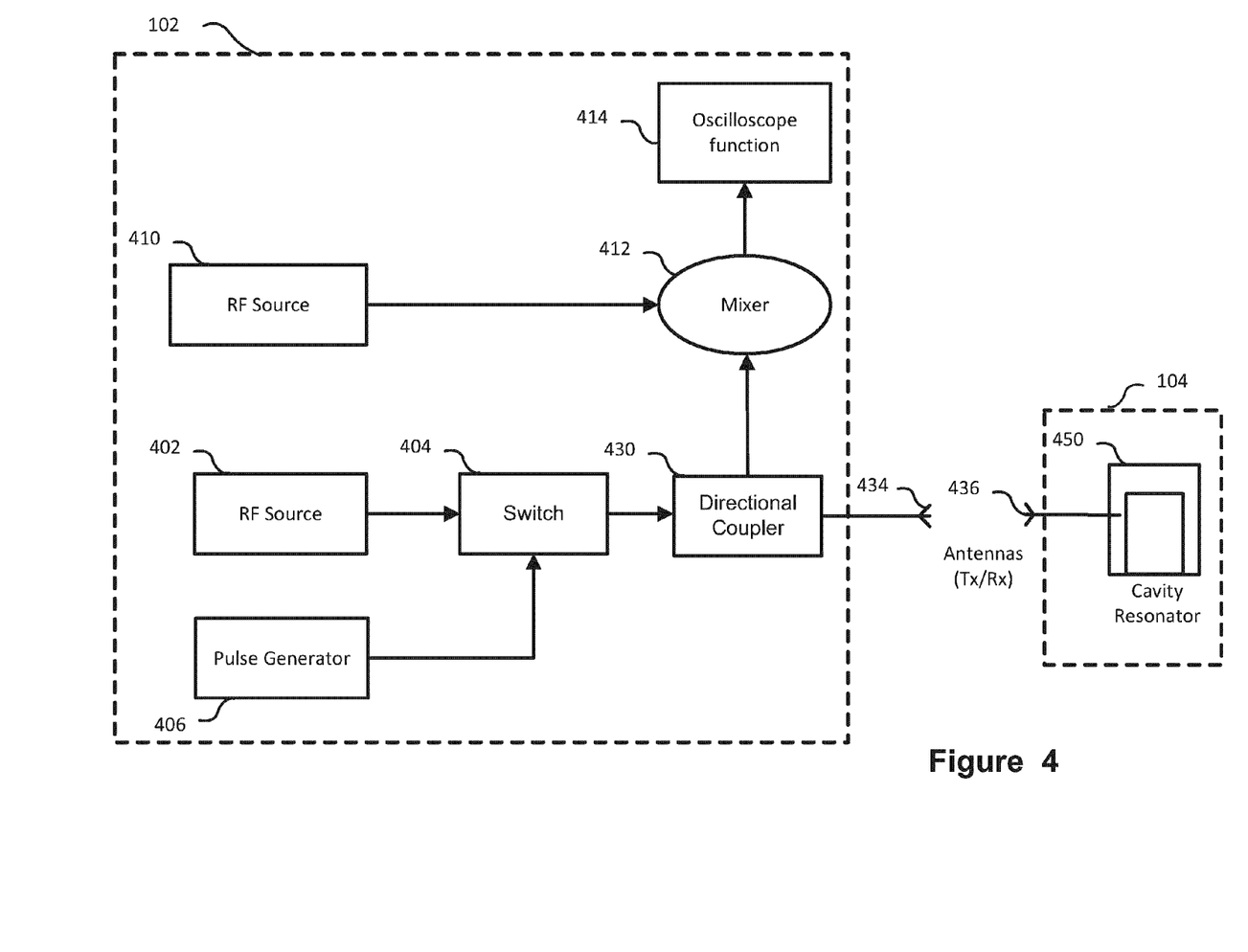
FIG. 4 shows an interrogation setup for fast sampling of the resonance frequency.

The interrogation system 102 facilitates a high sampling rate of the resonance frequency. A block diagram of the interrogation system 102 is illustrated in FIG. 4. A Radio Frequency (RF) signal 402 is switched 404 on and off in response to a pulse generator 406. The frequency of the RF signal is set to a value close to the resonance frequency of the resonator 450. The frequency of switching determines the measurement sampling rate of the sensor resonance frequency. During the on time of the switch 404, each pulse from pulse generator 406 of RF signal 402 is sent to the resonator 450 through the antennas 434 436 which will energize the resonator 450. While the switch 404 is turned off, the resonator 450 resonates at its resonance frequency. The ring back of the resonator 450 (which is at its natural frequency) is received by the interrogator antenna 434 and will be down converted by mixing by mixer 412 with the RF source signal 410 which is at a lower frequency than the transmitted frequency of source 402, such as but not limited to 20 MHz to 30 Mhz. This ring back is digitized on a fast sampling rate oscilloscope 410, or computing device providing processing equivalent. The directional coupler 430 separates the transmitted and received signals. By determining the time between peaks during ring back, the resonance frequency of the sensor at each sampling time can be estimated. By mapping the result to the corresponding electric field as was shown in FIG. 3d, the electric field variation in time is obtained. The measurement and mapping function of the oscilloscope 410 may be performed in a computing device function as part of the interrogator or be provided by an external component. The oscilloscope in the interrogation system can be replaced by a fast sampling FPGA-based system or similar, significantly reducing the weight and cost of the interrogation system and simplifying the operation of the sensor for the end user.

Figure 5A:
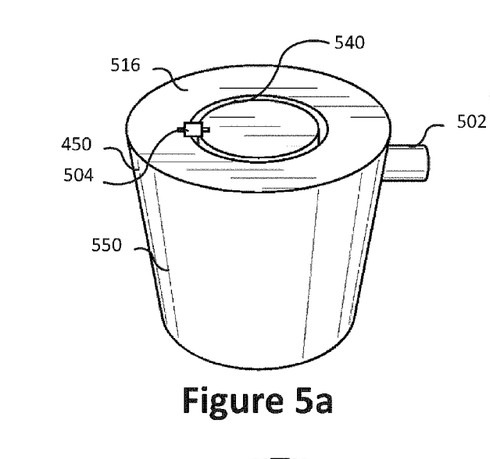
FIGS. 5a-5d shows a schematic representation of a sensor structure.
Figure 5B:
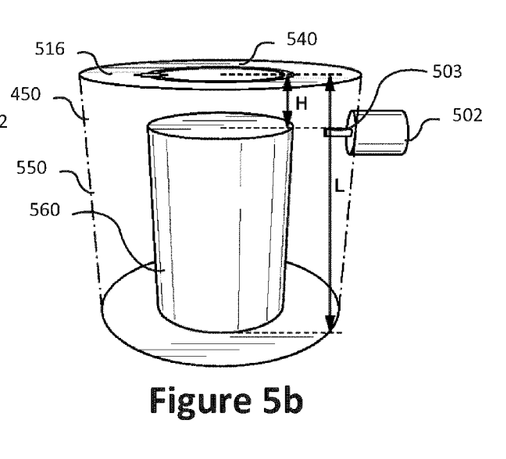
Figure 5C:
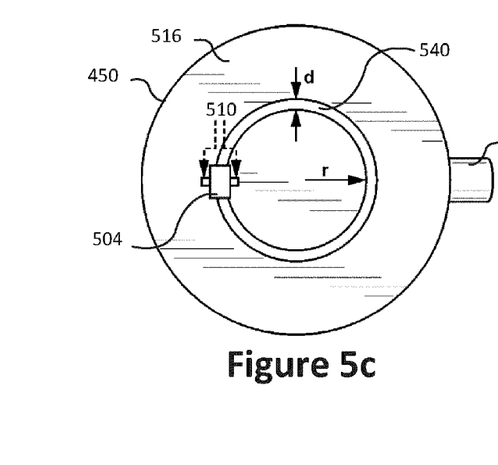
Figure 5D:
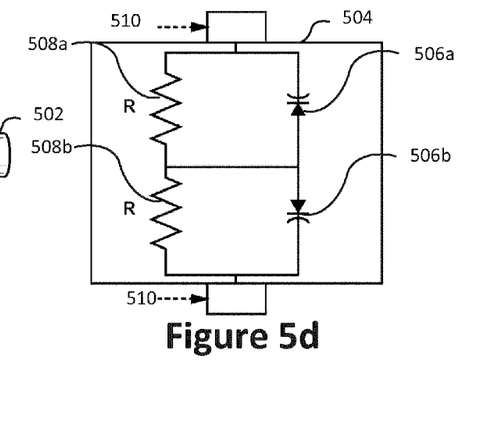

FIG. 5 shows a resonator structure where FIG. 5a shows and external side view, FIG. 5b shows an internal side view, FIG. 5c a top view and FIG. 5d shows details of the variable capacitance circuit shown in FIG. 5c. Interrogation distance and accuracy are controlled by the quality factor of the resonator. Higher quality factor decreases the damping, which lengthens the exponentially-decaying sine wave at the ring back and reduces the uncertainty of the measured resonance frequency. Therefore, low loss materials are used to fabricate the cavity. A coaxial transmission line cavity resonator is chosen for its high quality factor compared to those on PCBs. In the sensor structure shown in FIG. 5, important factors in determining the quality factor are the dimensions of the resonator and the radius of the isolated region. The sensitivity of the resonance frequency $f_r$ to the applied electric field $E_{AC}$ is defined as $\Delta f_r/\Delta E_{AC}$ which should also be maximized. The sensitivity is largely determined by the rate of change of capacitance with the maximum electric potential that can be applied over the terminals of the varactor.

The dimensions of the cavity resonator and the isolation ring 540 on the top loading PCB are designed to keep the resonance frequency in a desired frequency range, such as but not limited to for example the ISM band (2400 MHz to 2500 MHz) and also achieve the above mentioned properties, i.e. higher quality factor and higher sensitivity. This industrial, scientific, and medical radio band (ISM) band was chosen because the frequency range is high enough to utilize small antennas and with a large selection of device options. In disclosed design, some features have been chosen with fixed dimensions and the rest of the features can be chosen using finite element simulation results. SMV1231 from Skyworks™ can be utilized as the varactor for its low resistive loss although other similar varactors may be utilized. The inner and outer radii of the coaxial transmission line may be chosen based on the standard dimensions of available copper pipes although other dimensions may be utilized. The outer cylinder 550 has a radius for example of 14.29 mm on the inside and the inner cylinder 560 has an outside radius for example of 7.94 mm (standard 1.125" and 0.5" copper pipes). The material for constructing the resonator can be made of a highly conductive material, such as but not limited to copper or aluminum.

An subminiature version A (SMA) connector 502 is threaded through the wall 550 and the signal on the center conductor 503 capacitively couples the received energy from the antenna 436 into the resonator during the interrogation transmitting cycle. It also transfers the energy from the cavity to the antenna 436 when the RF pulse has been switched off and the energy from the cavity is being re-emitted (see FIG. 1). The overall quality factor decreases with deeper SMA pin 503 placement while the energy coupling increases. Increased coupling will decrease the loaded quality factor of the resonator as the loading effect increases. The desired depth of the SMA pin connector 503 can be determined by analyzing the S11 measurement results and setting the S11=−8 dB.

The ring gap 540 surrounding the isolated region can be milled on a top PCB 516. The varactors 506 are installed on the isolated region gap in parallel with resistors 508 that provide the discharging path. Surface-mount device (SMD) thick film resistors with a value of 475 MΩ can be used for example, the value of R determines the dynamic range. Soldering points providing circuit ports 510 of the circuit of the varactor and resistors span the isolation ring 540.

Referring to FIG. 5d, the two varactors 506a 506b with reverse polarities must be placed in series in order to capture both positive and negative half cycles of the external AC electric field. In each cycle, one varactor will be reversely biased and the other one will be conducting. Each varactor also requires a conducting path for the accumulated charges on the varactor capacitance in each cycle to be discharged in the next cycle. This path is provided by the resistors 508a 508b placed in parallel with each varactor 506a 506b respectively.

The gap distance, H, significantly affects the shift in resonance frequency and the quality factor. The length of the outer cylinder (L) can be chosen such that the resonance frequency of the cavity will remain in the specified frequency band such as the ISM band, although other frequency bands may be used. Simulation results of resonators of r+d=7 mm and d=1 mm in order to increase the resonance frequency shift a provided in Table 1. The maximum frequency shift reported in Table 1 are derived from direct application of a DC voltage (0 V to 5 V) over the varactor terminals of the resonator and measuring the S11 parameter using a network analyzer.

TABLE 1

Measured quality factor and maximum resonance frequency shift for three different L and H with fixed values of r = 6 mm, d = 1 mm and R = 475 MΩ

| L (mm) | H (mm) | $f_{res}$ (GHz) at $V_{Bias}$ = 0(V) | $\Delta f_{res}$ (MHz) for $V_{Bias}$= 0-5(V) | Quality factor |
|---|---|---|---|---|
| 29.5 | 5 | 2.449 | 11 | 462 |
| 28.0 | 4 | 2.404 | 13 | 240 |
| 25.5 | 3 | 2.413 | 19 | 100 |

The resonator loaded with a lumped capacitor representing the reverse biased varactor can be simulated in order to determine best values of r and d such that the resonance frequency shift increases for a given varactor capacitance change. The SMV1231 capacitance-voltage characteristics in the range of 0 V to 5 V of the reverse bias voltage shows a wide range of variation in the capacitance value, i.e. 2.35 pF to 0.683 pF.

Figures 6A, 6B, 6C:
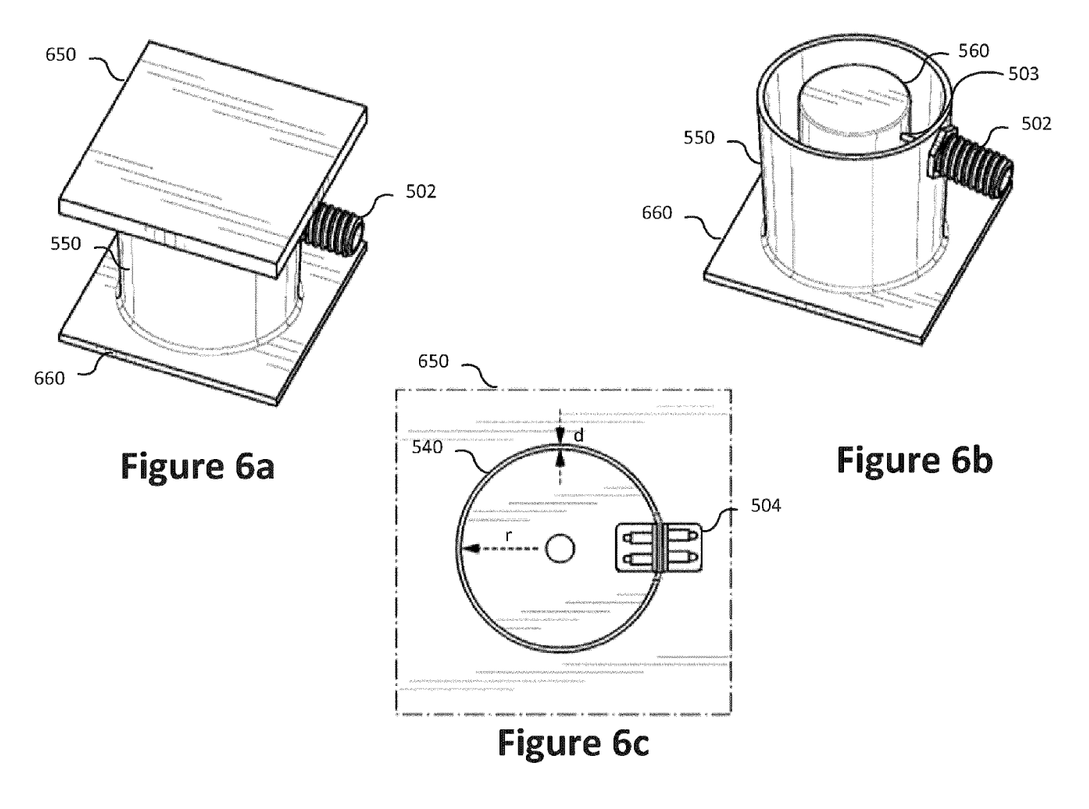
FIGS. 6a-6c shows a schematic representation of a resonator structure.

Referring to FIG. 6a, showing a top view of resonator 450, the ring gap is provided on a PCB 650 having the ring gap 540 covering the resonator cavity extends beyond the outer cylinder 550 of the body 550 of the sensor 450. The PCB 650 forms an equipotential surface, the measured electric field is strongest when the electric field lines are perpendicular to the top PCB 650 as in this situation the voltage induced in the isolated region is the highest. The bottom support surface 660 can be welded to the body 550 of the resonator or formed as part thereof. In FIG. 6b the PCB 650 is removed showing the inner cavity. FIG. 6c shows the underside of the PCB 650 providing a rectangular top surface covering the cavity.

Figure 7:
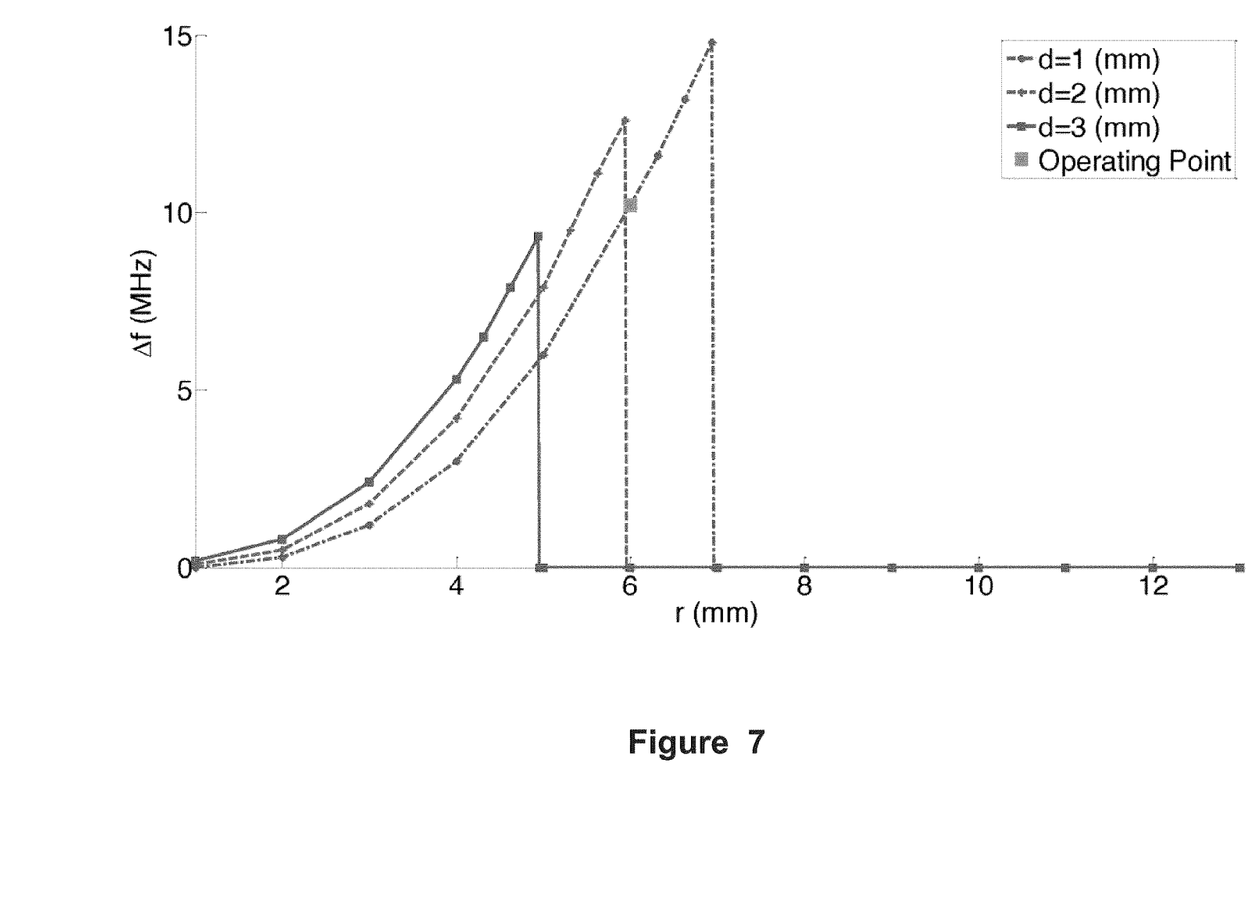
FIG. 7 shows maximum shift in resonance frequency versus the isolated region radius (r) for different isolated region gap (d)

Assuming L=29.5 mm and H=5 mm, which is chosen for the high quality factor from Table 1, the variation of the resonance frequency as a function of the ring radius surrounding the isolated region is shown in FIG. 7. The simulation results indicate that a smaller isolated region gap will result in a bigger resonance frequency shift. Further, the frequency variation is maximized for a specific isolation ring radius when the outer radius of the ring r+d equals the inside cylinder outer body radius of 7.94 mm.

Figure 8:
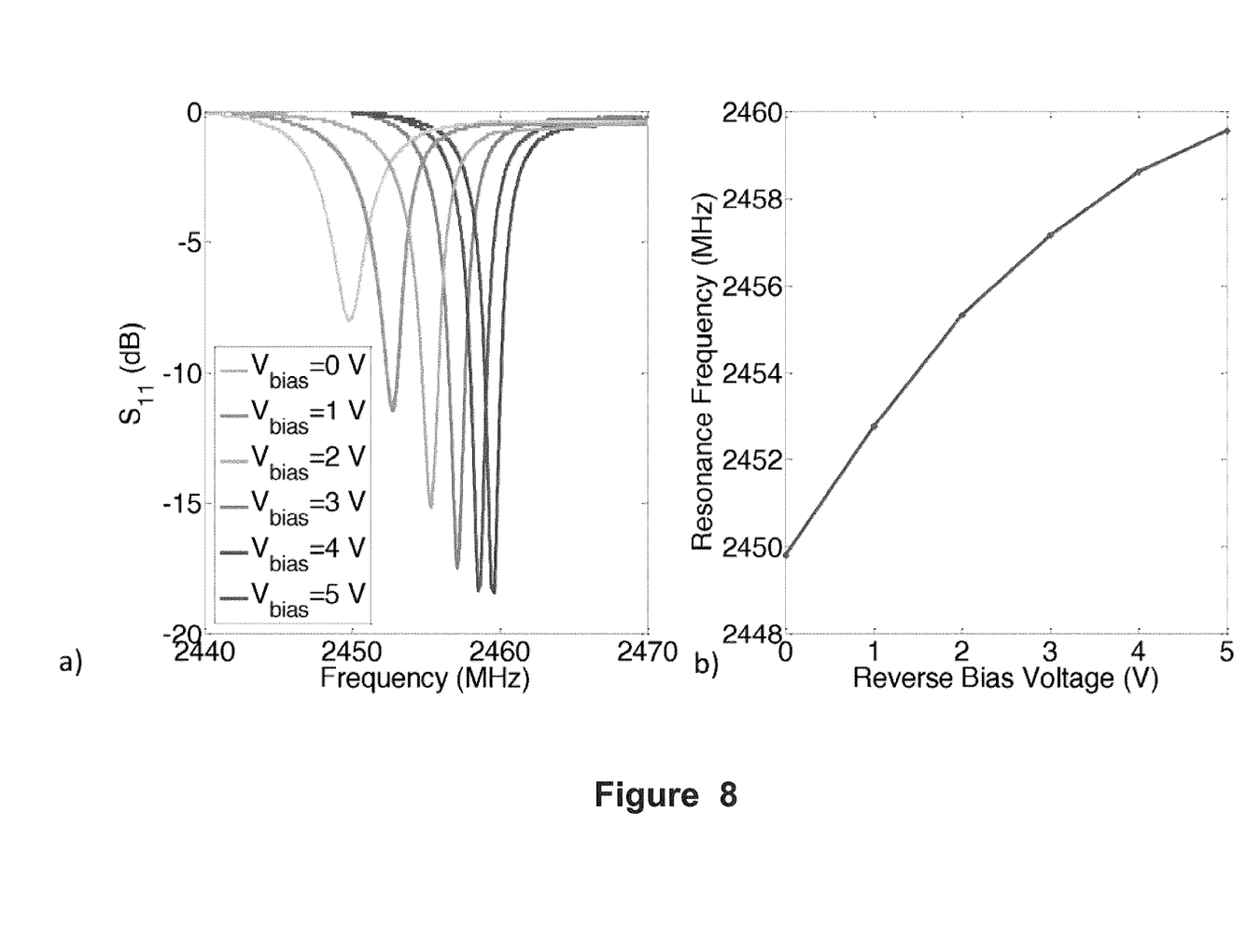
FIG. 8 shows S-parameter measurement results.
Figure 9:
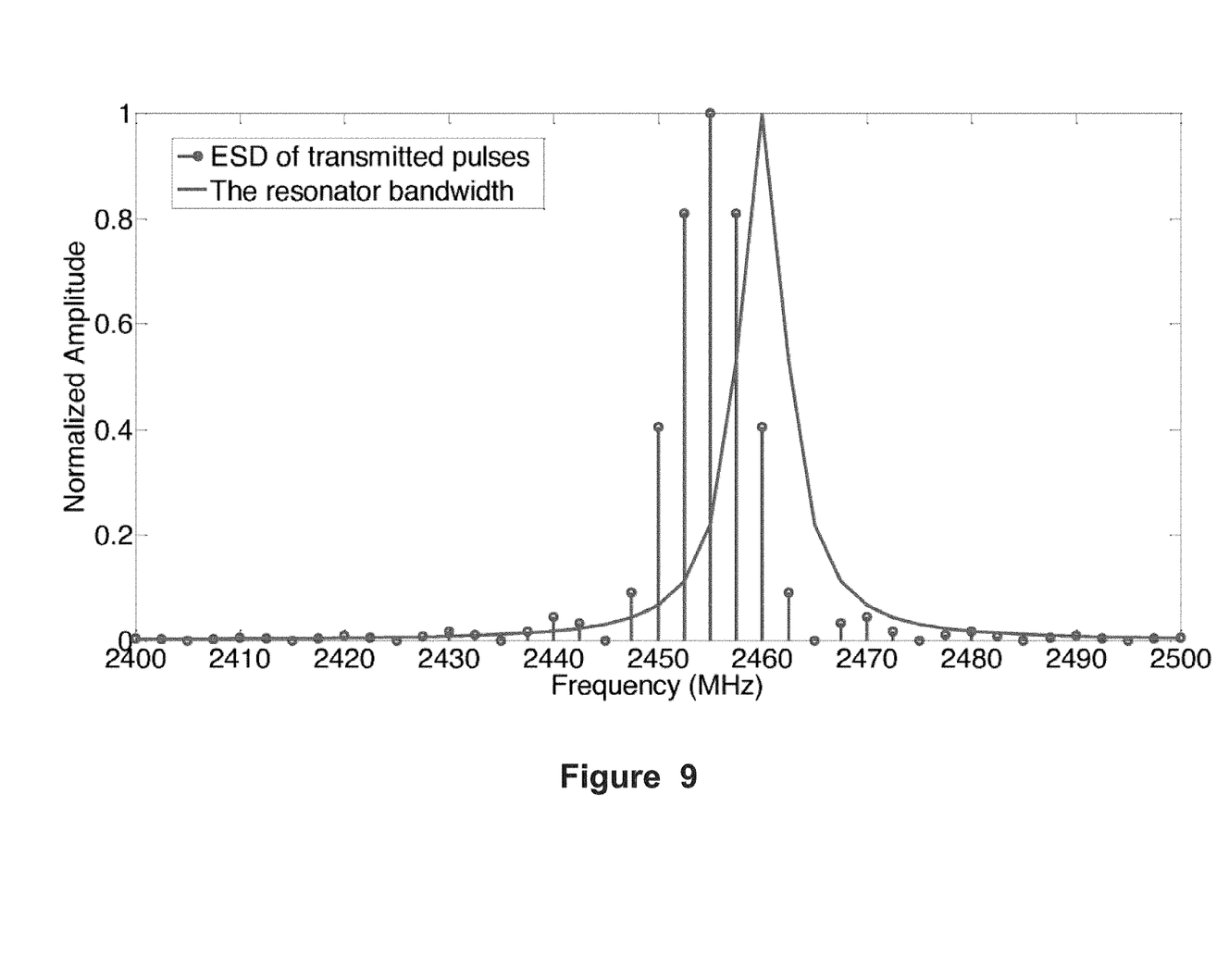
FIG. 9 shows an overlap of the energy spectral density (ESD) of the transmitted RF pulses and an approximation of the resonator bandwidth.

The frequency shift shown in Table 1 has been derived from S11 measurement of the cavity resonator using a network analyzer. A direct DC voltage was applied to the terminals of the varactors and the S11 was measured using a network analyzer. The variation of the measured S11 of the resonator with L=29.5 mm, H=5 mm, r=6 mm, and d=1 mm as a function of the bias voltage is shown in FIG. 8. The results of the S-parameter measurements represent the sensitivity of the sensor according to the voltage variation which is linearly related to the electric field variation. The resonance frequency shifts 11 MHz for a bias voltage variation of 0 V to 5 V The normalized energy spectral density of the RF transmitted pulses by the interrogator is a train of impulses in the frequency domain with an envelope of a sinc function as shown in FIG. 9. The resonator is assumed to be an ideal filter with a bandwidth of $f_r/Q$=5.3 MHz. For the interrogation method, the main lobe of the sinc function must have the maximum overlap with the resonator bandwidth. The sensor resonance frequency varies in the range 2450 MHz to 2460 MHz according to FIG. 8. Considering the bandwidth of 5.3 MHz for the resonator, the sinc function main lobe must approximately cover the range 2445 MHz to 2465 MHz. Therefore, the transmitted RF signal frequency is set to 2455 MHz to increase the coupling. The switching duty cycle ($T_0$) which determines the sinc function main lobe width is set to $T_0$=1/10 MHz=100 ns. The least amount of coupling is for the resonance frequencies of 2450 MHz or 2460 MHz corresponding to a minimum of 34% energy absorption from the antenna and an approximate energy loss of −4.7 dB.

Figure 10:
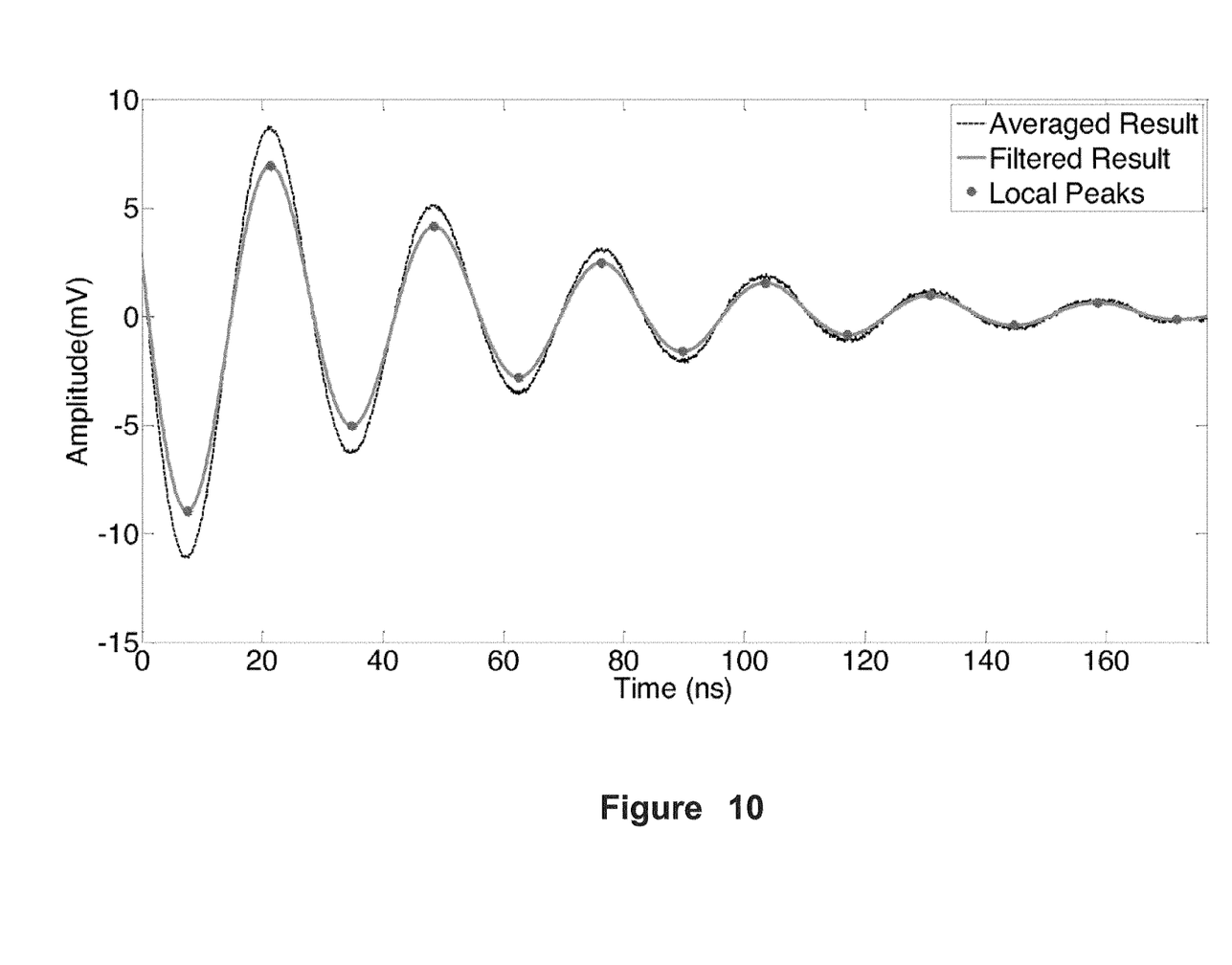
FIG. 10 shows ring back after transmitter is turned off.

In an embodiment the interrogator sends pulses of radio frequency signal with $f_{s1}$=2455 MHz to the resonator. A sample of the measured ring down waveform is shown in FIG. 10 with the peak locations identified. From the ring back time, the loaded quality factor of the resonator including the antenna loading can be determined as $$Q=\tau \pi f_r=(60ns)\times\pi\times(2.449\ GHz)=462$$

In this equation, $\tau$ is the ring back time constant and Q is the quality factor. The value of $\tau$=60 ns represents the worst case scenario derived from the measurements. Allowing $T_0$=100 ns=1.7 $\tau$ for excitation and 5 $\tau$=300 ns for the resonator ring back to damp, the resonator is energized to 81.1% and de-energized to 99.3% of its initial energy. There is a −0.9 dB loss due to the small energizing and de-energizing time in addition to −4.7 dB loss caused by the spectral overlap. The acceptable repetition rate must be close to less than $$f_{rep} = \frac{1}{T_0 + 5\tau} = \frac{1}{100\ ns + 5\times 60\ ns} = 2.5\ MHz$$

In order to reduce the noise effect, 50 consecutive samples averaged, reducing the effective interrogation sampling r to $f_{si}$=$f_{rep}$/50=50 kHz which is still much higher than required sampling rate of 600 Hz for the measurement of AC 60 Hz electric field.

The resonance frequency of the sensor is not highly dependent on temperature changes. With zero-bias on the varactors, varying the temperature from −4° C. to +60° C. can show an approximate shift of 1 MHz in the resonance frequency. To compensate for temperature dependence, a second resonator with similar structure and slightly different resonance frequency (≥10 MHz) from the electric field sensor can be mounted close to the sensor as a temperature sensor and interrogated simultaneously to compensate for the temperature-induced variation. The interrogation system has the potential to analyze multiple sensors simultaneously using proper filtering at the receiver.

There are two mechanisms that independently determine the bandwidth or the frequency range of AC electric field signals that can be recorded using the sensor. One is the speed of the interrogation system and algorithm and the other is the bandwidth limitation imposed by the sensor itself. The interrogation system is capable of delivering a readout in about 1/fsi=1/50 kHz=20 μs. Therefore, the interrogation system is able to measure transient signals (such as switching impulses) with rise times in the order of msec. The sensors upper cutoff frequency is limited by the operating frequency of the varactors which is less than 1 MHz. The lower cutoff frequency is determined by the reverse bias current of the varactor that is in the range of a few Hz.

Figure 11:
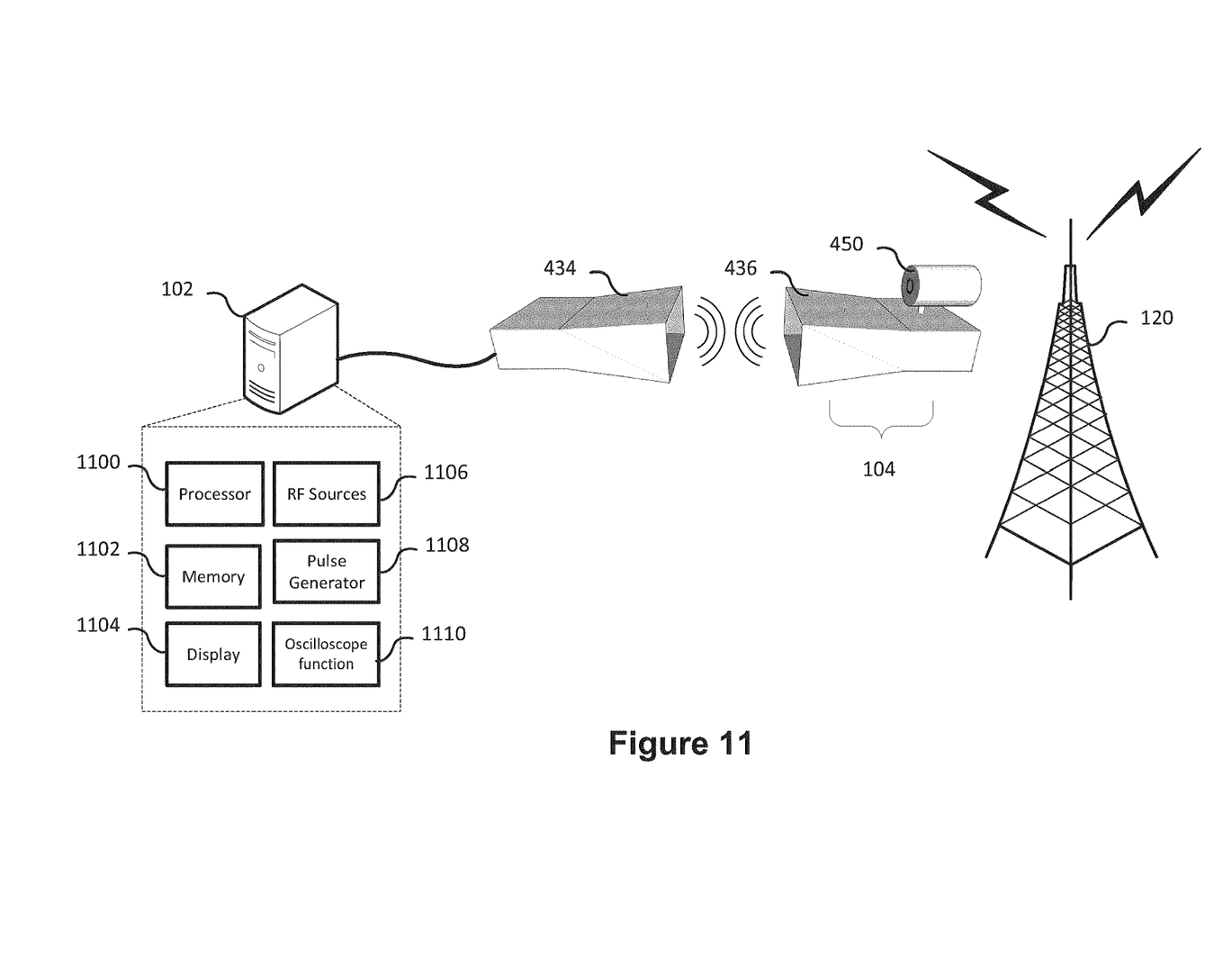
FIG. 11 shows the interrogation setup.

FIG. 11 shows the interrogation configuration. The resonator 450 is connected within the proximity of high voltage apparatus 120. The resonator 450 is connected to one of the antennas 436 through a coaxial cable. The interrogator 102 provides an RF source function, a pulse generator function and an oscilloscope function are sending and receiving signals via the other antenna 434. The interrogator 102 can also provide a processor 1100, memory 1102 and display 1104 for interfacing or providing with the RF sources 1106, pulse generator 1108 and osciliscope functions to generate 1110 the RF signals and analyze the received RF signals.

Figure 12:
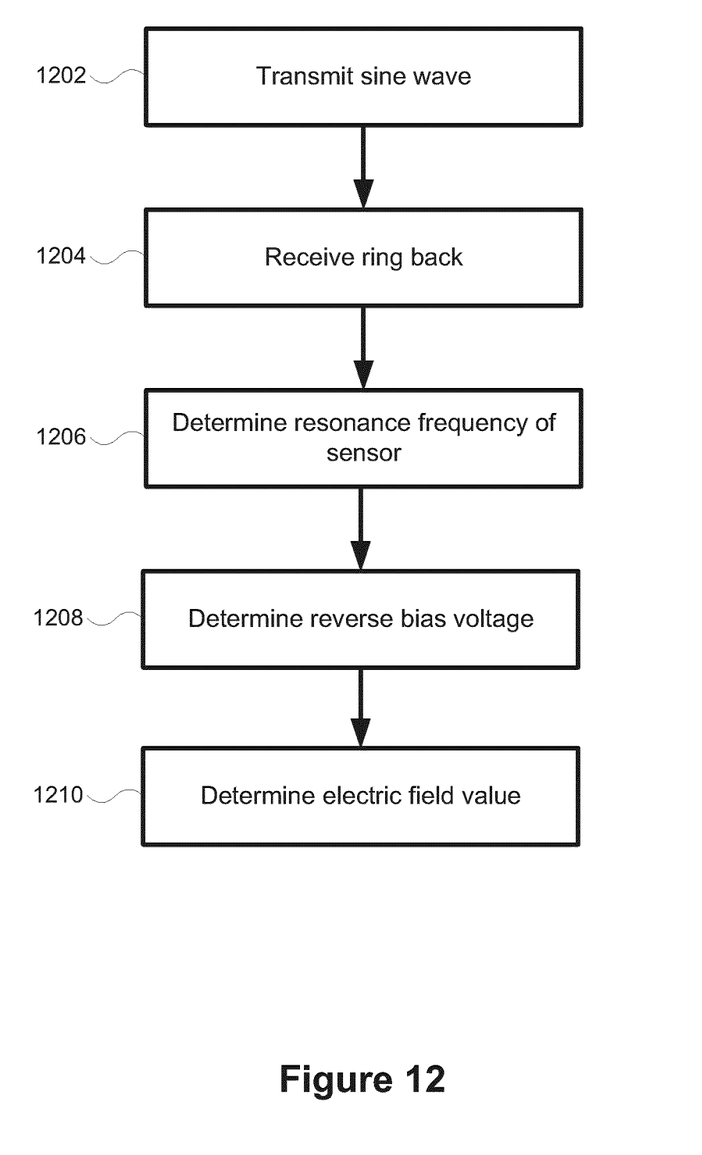
FIG. 12 is a method of measurement of AC electric field in the vicinity of high voltage apparatus.

FIG. 12 is a method of measurement of AC electric field in the vicinity of high voltage apparatus. A sine wave is transmitted from the interrogator (1202). A ring back is received from the resonator (1204). The resonance frequency of the sensor is determined (1206). A reverse bias voltage of the inducing electric field is determined from the received RF ring back signal and the determined resonate frequency (1208). An electric field measurement value is determined from the determined bias voltage (1210). The electric field measurement can be used for insulation defect detection or voltage measurement using a few sensors surrounding the high voltage apparatus and deriving the voltage on the apparatus by deriving the electric field profile.

Any processing of the disclosure may be implemented by causing a processor (e.g., a CPU inside a computer system), filed programmable gate array (FPGA), application specific integrated circuit (ASIC), a computer system or processing device to execute a computer program or perform processing functions. In this case, a computer program product can be provided to a processor using any type of non-transitory computer readable media. The computer program product may be stored in a non-transitory computer readable medium in the computer or the network device. Non-transitory computer readable media include any type of tangible storage media. Examples of non-transitory computer readable media include magnetic storage media (such as floppy disks, magnetic tapes, hard disk drives, flash memory, etc.), optical magnetic storage media (e.g. magneto-optical disks), compact disc read only memory (CD-ROM), compact disc recordable (CD-R), compact disc rewritable (CD-R/W), digital versatile disc (DVD), Blu-Ray™ disc (BD), and semiconductor memories (such as mask ROM, programmable ROM (PROM), erasable PROM), flash ROM, and RAM). The computer program product may also be provided to a computer or a network device using any type of transitory computer readable media. Examples of transitory computer readable media include electric signals, optical signals, and electromagnetic waves. Non-transitory computer readable media can provide

The invention claimed is:

1. A method of measurement of alternating current (AC) electric field in the vicinity of high voltage apparatus, the method comprising:
   transmitting radio frequency (RF) sine wave pulses to a passive sensor placed within an AC electric field, the passive sensor comprising:
     an inner cylinder and an outer cylinder comprising a coaxial cavity resonator having an air filled gap;
     a top surface comprises a printed circuit board material having a varactor thereon spanning a ring gap surrounding an isolated region coupling the inner and outer cylinders; and
     a coaxial connector on the outer cylinder for coupling to an antenna for receiving a wireless signal wherein the wireless signal comprising RF pulses for generating a ring back signal for measuring of the AC electric field;
   receiving an RF ring back signal from the passive sensor;
   determining a resonant frequency of the passive sensor;
   determining a reverse bias voltage of the inducing AC electric field from the received RF ring back signal and the determined resonant frequency; and
   determining an electric field measurement value from the determined reverse bias voltage.

2. The method of claim 1 wherein the varactor is located on the ring gap of a top surface connecting the inner and outer cylinder of the coaxial cavity resonator.

3. The method of claim 2 wherein the varactor comprises two varactors of different polarities.

4. The method of claim 3 wherein each half cycle of a sine wave one of the two varactors is reversely biased, the other varactor will not be able to discharge the accumulated charge during a previous half cycle through a reverse diode.

5. The method of claim 1 wherein determining the resonant frequency of the passive sensor is determined by characterisation of the passive sensor.

6. The method of claim 1 wherein the received RF ring back signal is mixed with an RF source signal having a frequency less than the RF sine wave pulses.

7. The method of claim 1 wherein a plurality of sensors surrounding the high voltage apparatus can derive a voltage on the high voltage apparatus by deriving an electric field profile.

8. A passive sensor for measurement of alternating current (AC) electric field in the vicinity of high voltage apparatus, the passive sensor comprising:
   an inner cylinder and an outer cylinder comprising a coaxial cavity resonator having an air filled gap;
   a top surface comprises a printed circuit board material having a varactor thereon spanning a ring gap surrounding an isolated region coupling the inner and outer cylinders; and
   a coaxial connector on the outer cylinder for coupling to an antenna for receiving a wireless signal wherein the wireless signal comprising radio frequency (RF) pulses for generating a ring back signal for measuring of the AC electric field.

9. The passive sensor of claim 8 wherein the inner and outer cylinders are made of a highly conductive material.

10. The passive sensor of claim 8 wherein the varactor comprises two varactors of different polarities and a resistor network.

11. The passive sensor of claim 8 wherein each half cycle of a sine wave one of the varactors is reversely biased, the other varactor will not be able to discharge the accumulated charge during a previous half cycle through a reverse diode.

12. The passive sensor of claim 8 wherein a resonate frequency of the coaxial cavity resonator is determined by characterisation of the resonator.

13. A system for measuring a high voltage alternating current (AC) electric field of a high voltage apparatus, the system comprising:
   a passive AC electric field sensor, placed in proximity to the high voltage AC electric field, for receiving radio frequency (RF) pulses and generating a ring back signal, the passive AC electric field sensor comprising:
     an inner cylinder and an outer cylinder comprising a coaxial cavity resonator having an air filled gap;
     a top surface comprises a printed circuit board material having a varactor thereon spanning a ring gap surrounding an isolated region coupling the inner and outer cylinders; and
     a coaxial connector on the outer cylinder for coupling to an antenna for receiving a wireless signal wherein the wireless signal comprising RF pulses for generating the ring back signal for measuring of the AC electric field; and
   an interrogation system for generating the RF pulses wireless sent to the passive AC electric field sensor and receiving the ring back signal from the passive AC electric field sensor and determining an electric field value for the inducing AC electric field.

14. The system of claim 13 wherein the coaxial cavity resonator has the varactor located on the ring gap of the top surface connecting the inner and outer cylinder of the coaxial cavity resonator.

15. The system of claim 14 wherein the varactor comprises two varactors of different polarities.

16. The system of claim 15 wherein each half cycle of a sine wave one of the two varactors is reversely biased, the other varactor will not be able to discharge the accumulated charge during a previous half cycle through a reverse diode.

17. The system of claim 13 wherein a resonate frequency of the passive AC field sensor is determined by characterisation of the passive AC field sensor.

18. The system of claim 13 wherein the received RF ring back signal is mixed with an RF source signal having a frequency less than the RF transmitter source frequency.

19. The system of claim 13 wherein the transmitted RF ring back signal is in an ISM frequency band.

20. The system of claim 13 wherein AC electric field measurement can be utilized for insulation defect detection.

21. The system of claim 13 wherein a plurality of sensors surrounding the high voltage apparatus can derive a voltage on the apparatus by deriving an electric field profile.

* * * * *